United States Patent [19]

Webster et al.

[11] Patent Number: 5,220,083
[45] Date of Patent: Jun. 15, 1993

[54] SYNTHESIS OF PERFLUOROPROPANE

[75] Inventors: James L. Webster, Parkersburg, W. Va.; Steven H. Swearingen, Wilmington, Del.; Douglas W. Bruhnke, Landenberg, Pa.; Leo E. Manzer, Wilmington, Del.; Elrey L. McCann, Mendenhall, Pa.

[73] Assignee: E. I. Du Pont de Nemours and Company, Wilmington, Del.

[21] Appl. No.: 826,296

[22] Filed: Jan. 28, 1992

Related U.S. Application Data

[63] Continuation of Ser. No. 734,016, Jul. 22, 1991, abandoned, which is a continuation of Ser. No. 452,403, Dec. 19, 1989, abandoned.

[51] Int. Cl.$^5$ .............................................. C07C 17/00
[52] U.S. Cl. ....................................... 570/169; 570/165
[58] Field of Search ............... 570/153, 161, 162, 166, 570/169, 168, 165

[56] References Cited

U.S. PATENT DOCUMENTS

| | | | |
|---|---|---|---|
| 2,755,313 | 7/1956 | Calfee | 570/166 |
| 3,258,500 | 6/1966 | Swamer et al. | |
| 3,436,430 | 4/1969 | Hall | 570/164 |
| 3,709,800 | 1/1973 | Fox | 570/164 |
| 3,712,931 | 1/1973 | Hamersma | 570/166 |
| 3,803,241 | 4/1974 | Stolkin et al. | |
| 3,865,885 | 2/1975 | Bruce | |
| 4,110,406 | 8/1978 | Anello et al. | |

FOREIGN PATENT DOCUMENTS

| | | |
|---|---|---|
| 1070929 | 6/1967 | United Kingdom . |
| 1077932 | 8/1967 | United Kingdom . |

Primary Examiner—Alan Siegel

[57] ABSTRACT

The present invention relates to syntheses of perfluoropropane— .e., octafluoropropane—from acyclic three-carbon hydrocarbons or partially or totally halogenated acyclic three-carbon hydrocarbons.

1 Claim, 1 Drawing Sheet

SYNTHESIS OF PERFLUOROPROPANE

This is a continuation of application Ser. No. 734,016 filed Jul. 22, 1991, now abandoned which is a continuation of application Ser. No. 07,452,403 filed Dec. 19, 1989, now abandoned.

FIELD OF THE INVENTION

The present invention relates to syntheses of perfluoropropane—i.e., octafluoropropane—from acyclic three-carbon hydrocarbons or partially or totally halogenated acyclic three-carbon hydrocarbons.

BACKGROUND OF THE INVENTION

Perfluoropropane, $C_3F_8$, is useful for etching silicon chips, as a refrigerant, as a gaseous dielectric, and as a propellant.

Vapor phase chlorofluorination of two-carbon hydrocarbons to make saturated halocarbons is known, but two-carbon hydrocarbons have only terminal carbons, while three-carbon hydrocarbons also have a secondary carbon, which has sharply different reactivity in reactions with halogens and halogen compounds.

Vapor phase chlorofluorination of higher hydrocarbons (containing three or more carbon atoms) or isopropyl fluoride is reported in U.S. Pat. Nos. 3,436,430, 3,865,885, and 4,110,406. The reactions described in these references gave almost exclusively unsaturated products.

The reaction of a chlorinated hydrocarbon with 1–8 carbon atoms with HF to substitute F for Cl is disclosed in U.S. Pat. No. 3,258,500.

SUMMARY OF THE INVENTION

The present invention provides a process for the preparation of perfluoropropane in a single reaction step which results in the production of the desired perfluoropropane in high yield.

Specifically, the instant invention provides a process for the preparation of perfluoropropane comprising reacting a member of the group consisting of propane, propylene, and partially or totally halogenated C-3 acyclic hydrocarbons with HF and $Cl_2$, at a temperature of 100°–550° C. in amounts such that the ratio of HF to $Cl_2$ is between 1 and 7, in the presence of a solid metal-containing salt or oxide catalyst; and recovering the perfluoropropane.

BRIEF DESCRIPTION OF THE DRAWING

The FIGURE is a graphical representation of the reaction conditions used in the present process and the products obtained.

DETAILED DESCRIPTION OF THE INVENTION

Definitions

Figure 1:
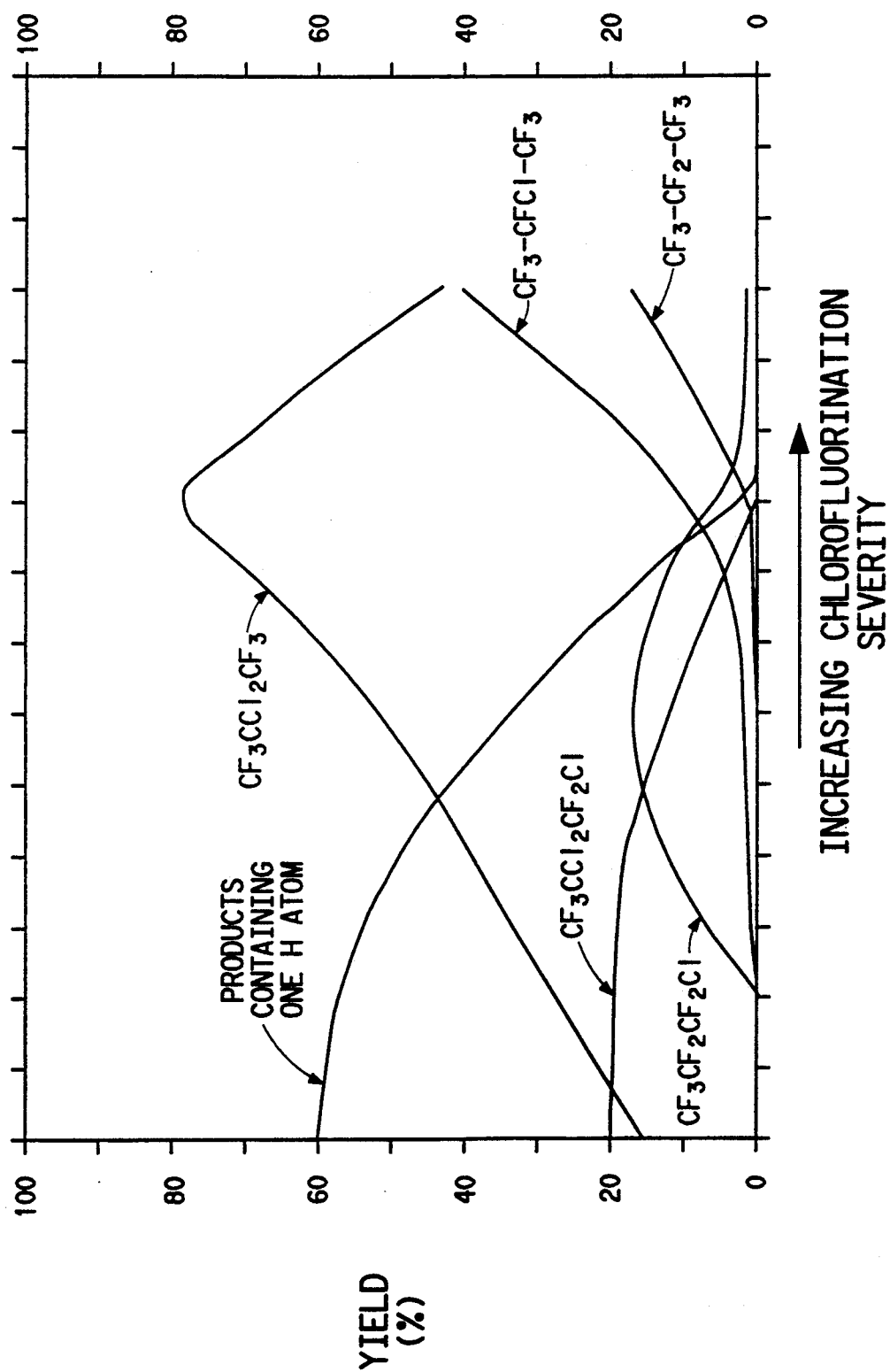

For the purpose of this disclosure:

Catalyst means a solid, metal-containing catalytic salt or oxide as charged to the reactor. In many of the reactions described, the catalyst undergoes unknown changes in composition during pretreatment and reaction steps.

Contact time means the volume of catalyst charged to the reactor in ml, divided by the sum of all gas flow rates, in ml/sec, as measured at standard temperature and pressure.

Halogen means Cl and F.

Chlorofluorination means reaction of propane, propylene, hexachloropropylene, and/or a halogenated three-carbon acyclic compound with a mixture of $Cl_2$ and HF.

In the following sequences of reactions, conventional procedures may be used for reactant and product isolation and, if desired, recycle. Especially useful techniques are fractional distillation, decantation, and partial condensation. It is possible not only to have a separate recovery system for each reaction, as is conventional, but in the case of the two major steps involved, chlorofluorination and fluorination with HF, it is possible to combine the product streams for product isolation.

Chlorine, HF, and HCl are separated by conventional methods. Thereafter, the lowest boiling material (after the removal of C-1 and C-2 by-products) is $C_3F_8$, which is the desired final product. Next lowest boiling among saturated products is the intermediate $CF_3$—$CFCl$—$CF_3$. Intermediates containing two or more chlorine atoms boil higher, and all intermediates may be recycled with or without isolation.

The catalysts which are effective for chlorofluorination include compounds of the metallic elements. At reaction conditions they may be in the form of their fluorides, oxyfluorides, chlorides, oxychlorides or oxides, but in the catalysts charged to the reactor they may be in the form of any compounds convertible to the above compounds under reaction conditions, such as pseudohalides and acid salts. They may be used either alone or in combination and in the presence or absence of a support such as, but not limited to, low alkali metal content elemental carbon. Some minerals such as ceria and didymia contain mixtures of rare earths such as La, Sm, Nd, and Pr, and the salts of these minerals may be more practical to use than those of the pure elements.

Preferred catalysts for the chlorofluorination to make $CF_3$—$CFCl$—$CF_3$ and $C_3F_8$ are chromium-containing catalysts such as $Cr_2O_3$, $Cr_2O_3$ on alumina, $Cr(OH)_3$ and $Cr_{0.5}Mn_{0.5}O_2$. Acceptable results can be obtained with other metal-containing catalysts, provided the temperature, contact time, and other reaction conditions are suitably selected.

A temperature may be employed of between 100° C. and 550° C. However, the preferred temperature is 200° C. to 480° C. The most preferred temperature is 350° C. to 480° C. The temperature used depends on the contact time chosen, the catalyst used, and the time the catalyst has been on stream.

In chlorofluorination the concentration of chlorine in relationship to propane/propylene may vary over a fairly broad range. Illustratively, mole ratios of chlorine to propane may be from 8 to 25, with the preferred range being 9 to 20 and the most preferred range being 10 to 14. Mole ratios of chlorine to propylene may be from 7 to 25, with a preferred range being 7 to 20 and the most preferred range being 8 to 16.

In chlorofluorination the concentration of hydrogen fluoride in relationship to propane/propylene may vary over a fairly broad range, depending on the product desired. When perfluoropropane is being made directly, a relatively large amount of HF is preferred. Illustratively, mole ratios of hydrogen fluoride to propane/propylene may be from 3 to 300, with a preferred range of 20 to 60, and most preferred range of 30 to 50. The heat of chlorofluorination is much lower if the starting material is highly halogenated (e.g. $C_3Cl_6$) instead of propane/propylene, therefore, it is not necessary to use as much HF as a heat sink in the adiabatic chlorofluorination step.

The above discussion of reactant ratios is based on the assumption that partially halogenated products are not being recycled. The large amounts of HF and $Cl_2$ are preferred because the chlorofluorination reaction is so exothermic that it is desirable to operate adiabatically, with large amounts of cooled recycle feed absorbing the heat given off by the chlorofluorination reaction.

The ratio of HF to chlorine can be varied over the range of 1-7. It is preferable to use higher HF:chlorine ratios, such as 2-7, to make highly fluorinated products ($C_3F_8$ and/or $CF_3$—$CFCl$—$CF_3$).

In practice, it is convenient to recycle halocarbons that are not fluorinated to the desired degree, so that they will be converted to desired products. Underfluorinated byproducts can be recycled, with or without added propylene.

In addition to propane, propylene, recycled intermediates, hexachloropropylene, perchloropropane, and mixtures thereof, it is also possible to feed to the chlorofluorination reaction a partially halogenated three-carbon acyclic compound. As one example, 1,2-dichloropropane is readily available and can be used as the starting material, alone or with other feed materials specified above.

The reaction pressure is not critical. Preferably it may be between 1 and 40 atmospheres. About 20 atmospheres is preferred to allow easy separation of HCl from the halocarbons without requiring compression.

The yield of desired products will be determined to a large extent by the temperature and contact time of the reactant materials with the catalyst. Contact times of the order of 300 seconds or less are suitable. Preferred contact times are 0.01 to 100 seconds. Most preferred contact times are 0.05 to 15 seconds.

When catalysts are relatively inactive or when mild chlorofluorination conditions of temperature, contact time, and reactant ratios are used, the products obtained may still contain hydrogen, and are often unsaturated. Somewhat more strenuous conditions or more active catalysts give unsaturated products in which all hydrogen atoms have been replaced with halogen. The still more strenuous conditions and/or more active catalysts employed in the process of the present invention give saturated halocarbons which are rich in Cl. The most strenuous conditions or active catalysts give highly fluorinated halopropanes such as $CF_3$—$CFCl$—$F_3$ or $C_3F_8$. In all cases, recycle of under-chlorofluorinated three-carbon intermediates results in further chlorofluorination and eventually in highly fluorinated halopropanes. The preferred temperature, contact time, and reactant ratios depend on the catalyst in use, how long it has been on stream, and the chlorofluoropropanes desired to be produced.

FIG. 1 illustrates schematically how the conversion to the various chlorofluoropropanes referred to in the previous paragraph changes with increasing severity of conditions when propylene is chlorofluorinated over $CrO_x$ on $Cr_2O_3$; the severity of conditions was varied by changing contact time or temperature. At 350°-500° C., chloroflorination gives increasing amounts of $CF_3$—$CFCl$—$CF_3$ and perfluoropropane and substantially no degradation products. As those skilled in the art appreciate, there is a relationship between catalyst activity, temperature, pressure, and contact time such that more active catalyst and higher pressure permit operation at lower temperature and shorter contact time.

While many of the experiments reported used propylene as the feed hydrocarbon, propane can be used with similar effectiveness.

General Procedure for Chlorofluorination

The reactor was an Inconel tube with an outside diameter of 0.5 inch (1.27 cm), shaped like a squared U. It was charged with the desired amount of catalyst, usually 20 ml, and purged with nitrogen. The reactor temperature was increased via a heated fluidized sand bath to 450° C. The nitrogen flow was maintained through the reactor during the heating period. When a temperature of about 450° C. was achieved, the HF flow was initiated and the nitrogen flow was discontinued. The temperature was then adjusted to the desired value. The HF flow was decreased to the desired value followed by initiating the chlorine and propane (or propylene) flow at the desired value. Alternatively, after heating the catalyst at 450° C., the temperature was lowered to 150° C. A $N_2$/HF flow was started over the catalyst and the temperature slowly raised to the reaction temperature.

General Procedure for Product Analysis

Product analysis was achieved by gas chromatography using a 3 m column from Supelco packed with 5% Krytox ® fluorinated oil supported on Carbopack ® B graphitized carbon black. Sample injection was accomplished by an on line sample valve. The analysis was done at 70° C. for 8 minutes followed by temperature programming at 8 degrees per minute up to 200° C. and held at 200° C. for an additional 16 minutes. Product analyses are reported as relative area %.

General Procedure for Preparation Catalyst $MCl_x/C$ (CFP herein represents carbon, M represents metal, and x represents the valence of M)

The desired amount of metal chloride was dissolved in 35 to 75 ml of water and the entire solution poured over 40 cc of commercial carbon granules (Girdler 411, 0.32 cm pellets). The resulting mixture was allowed to stand at room temperature for one hour and was then placed in a vacuum oven at 110° C. for 16 to 24 hours to remove the water. The catalyst was then pretreated by heating in an atmosphere of nitrogen gas at 450° C. followed by heating in HF at 450° C. prior to its use as a chlorofluorination catalyst.

Catalyst Preparation

The following catalysts were prepared by the general procedure for $Mcl_x/C$:

| Catalyst | Starting Material |
| --- | --- |
| $FeCl_3/C$ | 39.7 g $FeCl_3.6H_2O$/35 cc $H_2O$ |
| $ZnCl_2/C$ | 20.44 g $ZnCl_2$/75 cc $H_2O$ |
| $RhCl_3/C$ | 2.0 g $RhCl_3$/75 cc $H_2O$ |
| $LaCl_3/C$ | 62.43 g $LaCl_3.7H_2O$/75 cc $H_2O$ |
| $CrCl_3/C(.01X)$ | 0.29 g $CrCl_3.6H_2O$/60 cc $H_2O$ |
| $CrCl_3/C(1X)$ | 39.17 g $CrCl_3.6H_2O$/60 cc $H_2O$ |
| $NdCl_3/C$ | 57.39 g $NdCl_3.6H_2O$/75 cc $H_2O$ |
| $CeCl_3/C$ | 57.41 g $CeCl_3.8H_2O$/75 cc $H_2O$ |
| $YCl_3/C$ | 48.54 g $YCl_3.6H_2O$/75 cc $H_2O$ |
| $PrCl_3/C$ | 56.86 g $PrCl_3.6H_2O$/75 cc $H_2O$ |
| $SmCl_3/C$ | 58.37 g $SmCl_3.2O$/75 cc $H_2O$ |
| $(ZnCl_2 + CoCl_2)/C$ | 30 g $ZnCl_2$/35 g $CoCl_2.6H_2O$/80 cc $H_2O$ |
| $(CuCl_2 + CoCl_2)/C$ | 2.56 g $CuCl_2.2H_2O$/35.0 g $CoCl_2.6H_2O$/75 cc $H_2O$ |

-continued

| Catalyst | Starting Material |
| --- | --- |
| (KCl + CoCl$_2$)/C | 1.12 g KCl/35 g CoCl$_2$.6H$_2$O/75 cc H$_2$O |
| (LaCl$_3$ + CoCl$_2$)/C | 5.57 g LaCl$_3$.7H$_2$O/35 g CoCl$_2$.6H$_2$O/75 cc H$_2$O |

The CrCl$_3$/C catalyst was 29% CrCl$_3$ on carbon.

Preparation of CoO/Cr$_2$O$_3$

Cr$_2$O$_3$, 100 g, was slurried in a solution of 4.94 g of cobalt nitrate in 500 ml of distilled water for 30 minutes. The water was then removed from the solution via a rotary evaporator and the crude catalyst was dried in a vacuum oven and then heated at 450° C. for one hour.

Preparation of NiO/Cr$_2$O$_3$

Cr$_2$O$_3$, 100 g was slurried in a solution of 5.0 g of nickel nitrate in 500 ml of distilled water for 30 minutes. The water was then removed from the solution via a rotary evaporator and the crude catalyst was dried in a vacuum oven and then heated at 450° C.

Preparation of Cr-oxide on Alumina

CrCl$_3$.6H$_2$O, 134 g, was dissolved in 1000 cc H$_2$O. To this solution was added 45 g of low alkali metal content Al$_2$O$_3$. The slurry was stirred and heated to 90° C. The pH of the hot solution was adjusted to 9 with concentrated ammonium hydroxide. The solution was stirred for one hour at 90° C. and then allowed to cool to room temperature. The crude solid was filtered, washed five times with 100 cc of H$_2$O and dried in a vacuum oven at 110° C. The catalyst was mixed with 1-5 wt % "Sterotex" powdered lubricant (registered trademark of Capital City Products Co, Columbus, Ohio, division of Stokely-Van Camp, for its edible hydrogenated vegetable oil) to give ⅛- diameter ×3/16" long cylindrical pellets from a Stokes tablet machine.

Preparation of Cr-oxide/AlF$_3$

CrCl$_3$.6H$_2$O, 134 g, was dissolved in 1000 cc H$_2$O. To this solution was added 45g of AlF$_3$. The slurry was stirred and heated to 90° C. The pH of the hot solution was adjusted to 9 with concentrated ammonium hydroxide. The solution was stirred for one hour at 90° C. and then allowed to cool to room temperature. The crude solid was flitered, washed five times with 100 cc of H$_2$O and dried in the vacuum oven at 110° C. The catalyst was mixed with 1-5 wt % "Sterotex" powdered lubricant to give ⅛" diameter× 3/16" long cylindrical pellets from a Stokes tablet machine.

Preparation of RhCl$_3$/CR$_2$O$_3$

Cr$_2$O$_3$, 100 g, was slurried in a solution of 2.6 g of RhCl$_3$ in 500 ml of distilled water for 30 minutes. The water was then removed from the solution via a rotary evaporator and the crude catalyst was dried in a vacuum oven and then fired at 400° C. for one hour.

Preparation of Cr$_{0.5}$Mn$_{0.5}$O$_2$

Cr(NO$_3$)$_3$.9H$_2$O, 400.15 g, and 287.06 g of Mn(NO$_3$)$_2$.6H$_2$O was dissolved in 1000 cc H$_2$O. The pH of the solution was adjusted to 9 with concentrated ammonium hydroxide. The crude solid was collected by filtration and dried in the vacuum oven and fired overnight at 500° C. The catalyst was mixed with 1-5 wt % "Sterotex" powdered lubricant to give ⅛" diameter ×3/16 " long cylindrical pellets from a Stokes tablet machine.

Preparation of La$_{0.8}$Ce$_{0.2}$CrO$_3$

La(NO$_3$)$_3$.6H$_2$O, 346.4 g, 86.8 g of Ce(NO$_3$)$_3$.6H$_2$O and 400.15 g of Cr(NO$_3$)$_3$. 9H$_2$O were dissolved in 1000 cc H$_2$O. The pH of the solution was adjusted to 9 with concentrated ammonium hydroxide. The crude solid was collected by filtration, washed with water and dried in the vacuum oven. The catalyst was fired at 600° C. for four days with daily grinding and mixing. The catalyst was mixed with 1-5 wt % "Sterotex" powdered lubricant to give ⅛ diameter×3/16" long cylindrical pellets from a Stokes tablet machine.

Preparation of Zr$_{0.5}$CR$_{0.5}$O$_{1.5-2.0}$

ZrO(NO$_3$).xH$_2$O, 100 g, and 159 g of Cr(NO$_3$)$_3$.9H$_2$O was dissolved in 2750 cc of H$_2$O. The pH of the solution was adjusted to 9 with concentrated ammonium hydroxide while vigorously stirring the solution. The crude solid was collected by filtration, washed with water and dried in the vacuum oven. The catalyst was fired at 500° C. overnight. The catalyst was mixed with 1-5 wt % "Sterotex" powdered lubricant to give ⅛" diameter×3/16" long cylindrical pellets from a Stokes tablet machine.

Preparation of La$_{0.7}$Sr$_{0.3}$CrO$_{0.7}$F$_{0.6}$

La(NO$_3$)$_3$.6H$_2$O, 303.1 g, 400.2 g of CR(NO$_3$)$_3$.9H$_2$O was dissolved in 1000 cc of H$_2$O. The pH of the solution was adjusted to 9 with concentrated ammonium hydroxide. SrF$_2$, 37.7 g, was added and the slurry was stirred for 30 minutes. The crude solid was collected by filtration, washed with 500 cc of H$_2$O and dried in a vacuum oven. The catalyst was fired 4 days at 600° C. with daily grinding and mixing. The catalyst was mixed with 1-5 wt % "Sterotex" powdered lubricant to give ⅛" diameter×3/16" long cylindrical pellets from a Stokes tablet machine.

Preparation of CrO$_x$ on Cr$_2$O$_3$

In 2000 ml of water was dissolved 160 g CrO$_3$. Eight portions of 10 ml ethanol were added at 5-minute intervals, with stirring. The mixture was stirred for 4 hours, and then 80 ml more ethanol was added with stirring. The mixture was refluxed overnight with stirring. The entire mixture was evaporated to dryness in a rotary vacuum drier, allowing the remaining dissolved solids to deposit on the chromia gel. Then drying was completed in a vacuum oven at 110° C. Pellets 0.125" (3.18 mm) in diameter were formed after the addition of 1% "Sterotex" powdered lubricant.

Dehydration of Cr$_2$O$_3$ Catalysts

When hydrous chromium oxide is used in making a catalyst, that catalyst is preferably heated to 450° C. for about one hour with a flow of a gaseous diluent such as nitrogen, to dehydrate the hydrous chromium oxide before the catalyst is used.

CHLOROFLUORINATION EXAMPLES

In all of the Examples herein: Yield, as reported in the examples, is calculated from peak areas obtained in gas chromatographic analysis. This is a common technique in product identification, even though various compounds have somewhat different response factors.

Conversion of hydrocarbon in all chlorofluorination reactions is complete. Conversion to a particular product in the examples is calculated from peak areas obtained in gas chromatographic analysis.

Temperature in a tubular reactor of less than about 1 cm in diameter is measured with a thermocouple in the heat transfer medium outside the tube. Temperature in a tubular reactor of more than about 1 cm diameter is measured with a thermocouple in an internal well. In large scale reactors, there are several thermocouples in the well so that the temperature profile can be observed.

To make $C_3F_8$ and recyclable intermediates, propylene was chlorofluorinated over $CrO_x$ on $Cr_2O_3$ as shown in FIG. 1. The yield to $C_3F_8$ and recyclable intermediates was above 99.5%.

Example 1.

Propylene was chlorofluorinated in a 1 inch by 7 foot (2.54 cm by 2.1 m) Inconel tubular reactor, with excess HF to absorb most of the evolved heat, over Shepherd Chemical Company $Cr_2O_3.3H_2O$. Chlorofluorination was carried out at 380° C. and 115 psia (793 kPa) with a feed of 1 mol/hour propylene, 20 moles/hr chlorine, and 40 moles/hr HF. Yields were 25% to $C_3F_8$, 39% $C_3F_7Cl$, 27% $C_3F_6Cl_2$, 2% $C_3F_5Cl_3$, 0.01% $CF_5HCl_2$, and 0.8% $CF_3CF_2Cl$. Thus the yield to $C_3F_8$ and recyclable intermediates was 94%.

Example 82. Propylene was chlorofluorinated over $CrO_x/Cr_2O_3$ in a tubular reaction vessel at 445° C. at a contact time of 0.30 seconds, using a flow of 35 ml/minute HF, 15 ml/minute chlorine, and 1.0 ml/minute propylene. The product was 25% $C_3F_8$, 35% $C_3F_7Cl$, and 41% $CF_3$—$CCl_2$—$CF_3$, along with 0.4% low molecular weight degradation products. Thus the yield to $C_3F_8$ and recyclables was 99%.

Perfluoropropane is made directly when chlorofluorocarbons are recycled to the chlorofluorination.

We claim:

1. A process carried out in the vapor phase for the preparation of perfluoropropane consisting essentially of reacting a member of the group consisting of propane, propylene, and partially or totally halogenated C-3 acyclic hydrocarbons with HF and $Cl_2$, at a temperature of 100°-550° C. in amounts such that the ratio of HF to $Cl_2$ is between 1 and 7, in the presence of a solid metal-containing salt or oxide catalyst; and recovering the perfluoropropane.

* * * * *